United States Patent [19]

Pfaendler

[11] 4,431,588
[45] Feb. 14, 1984

[54] 3-SUBSTITUTED BICYCLIC AQETIDINONE DERIVATIVES

[75] Inventor: Hans-Rudolf Pfaendler, Liestal, Switzerland

[73] Assignee: Ciba-Geigy Corporation, Ardsley, N.Y.

[21] Appl. No.: 480,080

[22] Filed: Sep. 30, 1982

Related U.S. Application Data

[60] Division of Ser. No. 327,380, Dec. 4, 1981, which is a continuation-in-part of Ser. No. 171,521, Jul. 23, 1980, abandoned.

[30] Foreign Application Priority Data

Aug. 1, 1979 [CH] Switzerland .......................... 7077/79
Jul. 1, 1980 [CH] Switzerland .......................... 5083/80

[51] Int. Cl.$^3$ ................. C07D 205/08; C07D 515/04; A61K 31/425
[52] U.S. Cl. .............. 260/239 A; 260/245.3; 260/245.2 R; 424/270
[58] Field of Search .................................... 260/239 A

[56] References Cited

FOREIGN PATENT DOCUMENTS 1569234 6/1980 United Kingdom .

OTHER PUBLICATIONS

Lombardi et al. *Tet. Letters* 1979, pp. 3777–3880.
Pfaendler et al., Chem. Abs. 95, 150561j.
Pfaendler, Chem. Abs. 95, 81032y.
Pfaendler et al., J. Amer. Chem. Soc., 102, 2039, (1980).

*Primary Examiner*—Mark L. Berch
*Attorney, Agent, or Firm*—Irving N. Feit

[57] ABSTRACT

Subject of the present invention are compounds of the formula

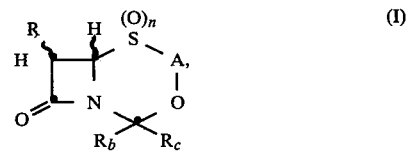

which can be used as intermediates, wherein
  R represents hydrogen or $R_a$, which represents an organic radical bonded to the ring carbon atom via a carbon atom,
each of the radicals
  $R_b$ and $R_c$ represents hydrogen or an organic radical bonded to the ring carbon atom via a carbon atom, it being possible for the two radicals to be bonded to one another,
  A represents a lower alkylene radical having 2 or 3 carbon atoms between the two hetero atoms, and
  n represents 0 or 2, the stereoisomers thereof and mixtures of these stereoisomers and also processes for the manufacture of such compounds of the formula I.

From compounds of the formula I it is possible to manufacture 6-$R_a$-2-penem-4-carboxylic acid compounds having antibiotio properties.

5 Claims, No Drawings

3-SUBSTITUTED BICYCLIC AQETIDINONE DERIVATIVES

This is a divisional of application Ser. No. 327,380 filed on Dec. 4, 1981, which in turn is a continuation-in-part of application Ser. No. 171,521, filed July 23, 1980, now abandoned.

The present invention relates to new compounds which can be used as intermediates for the manufacture of 6-substituted 2-penem-3-carboxylic acid compounds, wherein the 6-substituent is different from acylamino, and to processes for the manufacture of the new compounds.

Since the discovery of penicillin, numerous bicyclic thia-aza compounds having β-lactam structure have become known. A summary of earlier work is given in E. H. Flynn, "Cephalosporins and Penicillins", Academic Press, New York and London, 1972. More recent developments are described by J. Cs. Jászberényi et al., Progr. Med. Chem., Vol. 12, 1975, 395–477, P. G. Sammes, Chem. Rev. 1976, Vol. 76, No. 1, 113–155, and by various authors in an international symposium of the Chemical Society in Cambridge, England, June 1976 (subsequent publication: J. Elks, "Recent Advances in the Chemistry of β-lactam antibiotics", The Chemical Society, Burlington House, London, 1977).

In addition to the customary penam and cephem compounds, which carry an acylamino group in the 6- and 7-position, respectively, compounds have also become known that are unsubstituted in these positions, for example 3-carboxy-2,2-dimethylpenam (J. P. Clayton, J. Chem. Soc., 1969, 2123) and 3-methyl-4-carboxy-3-cephem (K. Kühlein, Liebigs Ann., 1974, page 369 and D. Bormann, ibid., page 1391). 3-Carboxy-2,2-dimethyl-penam compounds, that contain a 6α-chlorine or 6α-bromine grouping instead of the customary 6β-acylamino group, have become known through I. McMillan and R. J. Stoodley, Tetrahedron Lett. 1205 (1966), and J. Chem. Soc. C 2533 (1968), while corresponding 6α-hydroxy-, 6α-acetoxy- and 6α-phenoxyacetoxy-2,2-dimethylpenam-3-carboxylic acids have been described by D. Hauser and H. P. Sigg, Helv. Chimica Acta 50, 1327 (1967). However, none of these compounds has been known to have any antibiotic activity or at least any significant antibiotic activity.

6-Acylamino-2-penem-3-carboxylic acid compounds that have antibiotic activity and contain the 2-penem ring system are described in German Offenlegungsschrift (DOS) 2 655 298.

2-Penem-3-carboxylic acid compounds that contain in the 6-position a substituent that is different from an acylamino group and that are effective against both pencillin-sensitive and penicillin-resistant germs have previously not been published.

The 2-penem ring system has the formula

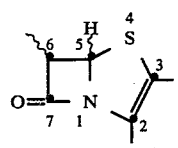

and can be named systematically 7-oxo-4-thia-1-azabicyclo[3,2,0]hept-2-ene. For the sake of simplicity, hereinafter it is called "2-penem", there being used the following numbering which is derived from penam and is customary in penicillin chemistry:

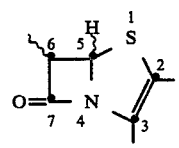

The 2-penem-3-carboxylic acid compounds can be manufactured in various ways using new intermediates. The present invention relates to new intermediates for the manufacture of 2-penemcarboxylic acid compounds and to processes for their manufacture.

The subject of the present invention relates to compounds of the formula

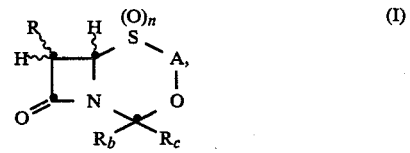

wherein
R represents hydrogen or $R_a$, which represents an organic radical bonded to the ring carbon atom via a carbon atom,
each of the radicals
$R_b$ and $R_c$ represents hydrogen or an organic radical bonded to the ring carbon atom via a carbon atom, it being possible for the two radicals $R_b$ and $R_c$ to be bonded to one another,
A represents a lower alkylene radical having 2 or 3 carbon atoms between the two hetero atoms, and
n represents 0 or 2,
stereoisomers thereof and mixtures of these stereoisomers, and processes for the manufacture of such compounds of the formula I.

An organic radical $R_a$ bonded to the ring carbon atom via a carbon atom is especially a saturated or unsaturated, optionally substituted, aliphatic, cyclo-aliphatic, cycloaliphatic-aliphatic, aromatic or arali-phatic hydrocarbon radical having up to 18, preferably up to 10 carbon atoms, or an optionally substituted heterocyclyl, heterocyclyl-lower alkyl, or an heterocyclyl-lower alkenyl radical having up to 10 carbon atoms and up to 4 ring hetero atoms from the group comprising nitrogen, oxygen and/or sulphur, especially optionally substituted lower alkyl or lower alkenyl, optionally functionally modified carboxy, or optionally substituted cycloalkyl cyclo-alkenyl, cycloalkyl-lower alkyl, cycloalkyl-lower alkenyl, cycloalkenyl-lower alkyl, phenyl, phenyl-lower alkyl or phenyl-lower alkenyl. Substituents of such radicals are, for example, optionally functionally modified, such as optionally etherified or esterified, hydroxy or mercapto groups, for example hydroxy, lower alkoxy, for example methoxy or ethoxy, lower alkanoyloxy, for example acetoxy or propionyloxy, hydroxysulphonyloxy that is present in salt form, halogen, for example chlorine or bromine, or lower alkylthio, for example methylthio, optionally functionally modified carboxyl groups, such as carboxyl, lower alkoxycarbonyl, for example methoxycarbonyl or ethoxycarbonyl, carbamoyl or cyano, also nitro, sulpho that is present in salt form, or optionally substituted amino, such as amino mono- or di-substituted by lower alkyl, for example methyl or ethyl, or by acyl, such as lower alkanoyl, for example acetyl, or amino di-substituted by lower alkylene, for example 1,4-butylene or 1,5-pentylene.

A lower alkyl radical $R_a$ contains up to 7, especially up to 4, carbon atoms and is, for example, methyl, ethyl, propyl, isopropyl, butyl, isobutyl, tert.-butyl or pentyl. Substituted lower alkyl $R_a$ is especially substituted methyl, ethyl or propyl, substituents being especially in the 1-position but also in the 2- or 3-position, and is, for example: hydroxyl-lower alkyl, such as hydroxymethyl, hydroxyethyl or hydroxypropyl; lower alkoxy-lower alkyl, such as lower alkoxymethyl, lower alkoxyethyl or lower alkoxypropyl, for example methoxymethyl, methoxyethyl or methoxypropyl; lower alkanoyloxy-lower alkyl, such as lower alkanoyloxymethyl, lower alkanoyloxyethyl or lower alkanoyloxypropyl, for example acetoxymethyl, propionyloxymethyl, acetoxyethyl or acetoxypropyl; hydroxysulphonyloxy-lower alkyl, such as hydroxysulphonyloxymethyl, hydroxysulphonyloxyethyl or hydroxysulphonyloxypropyl, that is present in salt form, for example in the form of an alkali metal salt, such as the sodium salt, or in ammonium salt form; halo-lower alkyl, such as halomethyl, haloethyl or halopropyl, for example chloroethyl or bromoethyl, or chloropropyl or bromopropyl; lower alkylthio-lower alkyl, such as methylthiomethyl, methylthioethyl, methylthiopropyl or tert.-butylthiomethyl; lower alkoxycarbonyl-lower alkyl, such as lower alkoxycarbonylmethyl or lower alkoxycarbonylethyl, for example methoxycarbonylmethyl, methoxycarbonylethyl, ethoxycarbonylmethyl or ethoxycarbonylethyl; cyano-lower alkyl, such as cyanomethyl or cyanoethyl; sulpho-lower alkyl, such as sulphomethyl, sulphoethyl or sulphopropyl, wherein the sulpho group is present in salt form, for example in the form of an alkali metal salt, such as the sodium salt, or alternatively in ammonium salt form; or optionally protected, for example also acetylated, amino-lower alkyl, such as aminomethyl, aminoethyl or aminopropyl.

A lower alkenyl radical $R_a$ contains from 2 to 7, especially from 2 to 4, carbon atoms and is, for example, vinyl, allyl or 2- or 3-butenyl. Substituted lower alkenyl can carry the same substituents as substituted lower alkyl.

An optionally functionally modified carboxyl group $R_a$ is a free or esterified or amidated carboxyl group, such as lower alkoxycarbonyl, for example methoxy-, ethoxy- or tert.-butoxy-carbonyl, aryl-lower alkoxycarbonyl, such as benzyloxy-, p-nitrobenzyloxy or diphenylmethoxy-carbonyl, aryloxycarbonyl, such as phenoxycarbonyl optionally substituted, for example, by halogen, such as chlorine, by lower alkoxy, such as methoxy, or by nitro, such as phenoxycarbonyl, o-, m- or p-chlorophenoxycarbonyl, pentachlorophenoxycarbonyl, o-, m or p-methoxyphenoxycarbonyl or pnitrophenoxycarbonyl, aminocarbonyl or substituted aminocarbonyl, such as aminocarbonyl mono- or di-substituted by lower alkyl, for example methyl or ethyl.

A cycloalkyl radical $R_a$ has, for example, from 3 to 7 carbon atoms and is, for example, cyclopropyl, cyclobutyl, cyclopentyl or cyclohexyl, while a cycloalkyl-lower alkyl radical $R_a$ contains, for example, from 4 to 7 carbon atoms and is, for example, cyclopropylmethyl, cyclobutylmethyl, cyclopentylmethyl or cyclohexylmethyl.

A cycloalkenyl radical $R_a$ is a corresponding cycloalkyl radical having one or optionally two C—C double bonds, such as cyclohexenyl, for example 1-cyclohexenyl, or cyclohexadienyl, for example 1,4cyclohexadienyl.

A cycloalkyl-lower alkenyl radical or cycloalkenyl-lower alkyl radical $R_a$ is, for example, cyclohexylvinyl or cyclohexylallyl, and cyclohexenylmethyl or 1,4-cyclohexadienylmethyl, respectively.

A phenyl radical or phenyl-lower alkyl radical, for example a benzyl radical or a 1- or 2-phenylethyl radical, $R_a$ is optionally substituted, preferably in the aromatic radical, for example by lower alkyl, such as methyl or ethyl, lower alkoxy, such as methoxy, or halogen, such as fluorine or chlorine, also by nitro or amino, it being possible for phenyl-lower alkyl to be substituted in the α-position, for example by hydroxy, hydroxysulphonyloxy, carboxy, sulpho or amino. carboxy, sulpho or amino.

In a heterocyclyl or heterocyclyl-lower alkyl radical $R_a$, heterocyclyl is a radical that is bonded via a carbon atom and is preferably of aromatic character, such as pyridyl, for example 2-, 3- or 4-pyridyl, thienyl, for example 2-thienyl, or furyl, for example 2-furyl, or a corresponding pyridyl-, thienyl- or furyl-lower alkyl radical, especially a pyridyl-, thienyl- or furyl-methyl radical, it being possible for heterocyclyl-lower alkyl to be substituted in the α-position, for example by hydroxy, hydroxysulphonyloxy, carboxy, sulpho or amino.

A phenyl- or heterocyclyl-lower alkenyl radical $R_a$ is a lower alkenyl radical substituted in the same manner as a corresponding lower alkyl radical, for example phenylvinyl or furylallyl.

A lower alkylene radical A is especially ethylene and 1,2-propylene, but can also be 1,3-propylene or 1,2- 2,3- or 1,3-butylene.

Organic radicals $R_b$ and $R_c$ are especially lower alkyl, for example methyl, ethyl, n-propyl or isopropyl, optionally substituted phenyl, or phenyl-lower alkyl, for example benzyl, or, if taken together, lower alkylene preferably having from 3 to 6 carbon atoms, for example 1,4-butylene or 1,5-pentylene.

The invention relates especially to compounds of the formula I wherein R represents hydrogen or $R_a$, $R_a$ being lower alkyl, lower alkenyl, hydroxy-lower alkyl, lower alkoxy-lower alkyl, lower alkanoyloxy-lower alkyl, aryl-lower alkoxycarbonyloxy-lower alkyl optionally substituted, for example by lower alkyl, lower alkoxy, halogen and/or nitro, or hydroxysulphonyloxy-lower alkyl that is present in salt form, A represents ethylene or 1,2-propylene, each of the radicals $R_b$ and $R_c$ is hydrogen, lower alkyl, phenyl-lower alkyl or phenyl or, if taken together, lower alkylene having up to 6 carbon atoms, for example 1,5-pentylene or 1,4-butylene, and n represents 0 or 2, the stereoisomers of compounds of the formula I and mixtures of these stereoisomers.

The invention relates especially to compounds of the formula I, wherein R represents hydrogen or the radical $R_a$, $R_a$ representing lower alkyl having up to 4 carbon atoms, for example methyl, ethyl, propyl or butyl, hydroxy- lower alkyl, especially 1-hydroxy-lower alkyl, having up to 4 carbon atoms, for example hydroxymethyl, 1-hydroxyethyl or 1-hydroxypropyl, lower alkenyl having up to 4 carbon atoms, lower alkoxy-lower alkyl especially 1-lower alkoxy-lower alkyl, wherein lower alkyl and lower alkoxy each contains up to 4 carbon atoms, for example methoxymethyl, 1-methoxyethyl or 1-methoxypropyl, lower alkanoyloxy-lower alkyl, especially 1-lower alkanoyloxy-lower alkyl, wherein lower alkanoyloxy and lower alkyl each contains up to 4 carbon atoms, for example acetoxymethyl, propionyloxymethyl or 1-acetoxyethyl, phenyl-lower alkoxycarbonyloxy-lower alkyl optionally substituted, for example by halogen and/or nitro, especially corresponding 1-phenyl-lower alkoxycarbonyloxylower alkyl, or hydroxysulphonyloxy-lower alkyl that is present in salt form, wherein lower alkyl contains up to 4 carbon atoms, especially 1-hydroxysulphonyloxy-lower alkyl, for example hydroxysulphonyloxymethyl, 1-hydroxysulphonyloxyethyl or 1-hydroxysulphonyloxypropyl, each present in salt form, each of the radicals $R_b$ and $R_c$ is hydrogen, or especially lower alkyl having up to 4 carbon atoms, or, if $R_b$ and $R_c$ are bonded, lower alkylene having from 3 to 6 carbon atoms, for example 1,5-pentylene or 1,4-butylene, and A represents ethylene or 1,2-propylene, and n can be 0 or 2, the stereoisomers of compounds of the formula I and mixtures of these stereoisomers.

The invention relates above all to compounds of the formula I wherein R represents hydrogen or the radical $R_a$, $R_a$ representing lower alkyl having up to 4 carbon atoms, especially methyl, lower alkenyl having up to 4 carbon atoms, or 1-hydroxy-lower alkyl having up to 4 carbon atoms, especially 1-hydroxyethyl, wherein the 1-hydroxy group can optionally be protected by an acyl group, such as the acyl radical of an organic carboxylic or sulphonic acid, such as optionally substituted lower alkanoyl, for example acetyl or trifluroacetyl, or phenyl-lower alkoxycarbonyl optionally substituted by halogen and/or nitro, for example benzyloxy carbonyl or optionally substituted phenylalkoxycarbonyl, for example p-nitrobenzyloxycarbonyl, each of the radicals $R_b$ and $R_c$ represents lower alkyl, especially methyl, or $R_b$ and $R_c$ together represent lower alkylene having up to 6 carbon atoms, especially 1,5-pentylene, and A is ethylene or 1,2-propylene, and wherein n is 0 or 2, the stereoisomers of compounds of the formula I and mixtures of these stereoisomers.

The compounds of the formula I are manufactured by reacting a compound of the formula II

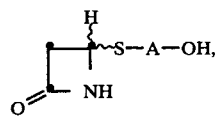

wherein A has the meaning given under formula I with a carbonyl compound of the formula

wherein $R_b$ and $R_c$ have the meanings given under formula I, or a derivative thereof, in the presence of an acid reagent and, if desired, a radical $R_a$ is introduced into a compound of the formula I thus obtained, wherein R represents hydrogen and converting a compound of the formula I thus obtained, wherein n represents O into a compound of the formula I in which n represents 2, and/or separating a mixture of isomers thus obtained into the individual isomers.

Carbonyl compounds of the formula III are preferably ketones, wherein each of the radicals $R_b$ and $R_c$ represents a monovalent organic radical, especially lower alkyl having up to 4 carbon atoms, for example methyl or ethyl, or aryl or aryl-lower alkyl having up to 10 carbon atoms, for example phenyl or benzyl, especially lower alkanones, for example acetone, or, if $R_b$ and $R_c$ taken together represent a bivalent organic radical, cyclic ketones, especially cycloalkanones, for example cyclohexanone, or also optically active ketones or aldehydes, for example camphor.

Derivatives of the carbonyl compound of the formula III are, for example, acetals or enol ethers, more especially acetone dimethyl ketal.

Acid reagents are strong and weak acids of the Bronsted type, for examine mineral acids, for example sulphuric acid or hydrochloric acid, organic acids, for example p-toluenesulphonic acid, or Lewis acids, for example boron trifluoride etherate, copper sulphate or iron(III) chloride.

The water that forms when reacting a compound of the formula II with a carbonyl compound of the formula III can be removed from the reaction mixture, for example by azeotropic distillation in the customary manner with the aid of a water separator.

Suitable solvents for this purpose are especially aromatic hydrocarbons, for example benzene or toluene.

The reaction is carried out preferably at elevated temperatures, for example from approximately 40° to approximately 150°, more especially at the boiling temperature of the particular reaction mixture.

Both antipodes of compounds of the formula II and their racemic or diastereoisomeric mixtures can be used in the reaction. The configuration of the chirality centres remains unchanged in the reaction.

Compounds of the formula II that have a further chirality centre in A can form diastereoisomeric mixtures. Such diastereoisomeric mixtures can be obtained, for example, by reacting a (4R,S)-acyloxyazetidinone of the formula IV with an antipode of a 2-mercaptopropan-1-ol, for example (2R)-2-mercaptopropan-1ol.

If desired, such a diastereoisomeric mixture can be separated using customary methods into the individual antipodes which can then be processed further in accordance with the above reaction, without alteration of the configuration, to form antipodes of the formula I.

An organic radical $R_a$ can be introduced into a compound of the formula I, in which R represents hydrogen, for example by treating a compound of the formula I that can be obtained according to the process and in which R represents hydrogen with a suitable metallating reagent, followed by a reactive compound corresonding to the organic radical $R_a$.

Suitable metallating reagents are substituted and unsubstituted alkali metal amides, alkali metal hydrides or alkali metal-lower alkyl compounds in which the alkali metal is sodium or especially lithium, for example sodium or lithium amide, lithium bis-trimethylsilylamide, sodium hydride, lithium hydride and preferably lithium diisopropylamide and butyllithium.

A reactive compound corresponding to the organic radical $R_a$ is, for example, a compound of the formula $R_a$—X, in which X represents a nucleofugal leaving group, for example a halogen atom, for example chlorine, bromine or iodine, or a sulphonyloxy group, for example mesyloxy or tosyloxy, or a carbonyl compound corresponding to the radical $R_a$, especially a ketone or an aldehyde compound of the formula $R_a'$—(C=O)—$R_a''$, in which $R_a'$ and $R_a''$, independently of one another, represent hydrogen or a group that, together with the carbinol group derived from the carbonyl group, forms a radical $R_a$. $R_a'$ and $R_a''$, independently of one another, are preferably hydrogen or lower alkyl.

Solvents that are suitable for the metallating reaction must not contain active hydrogen and are, for example, hydrocarbons, for example hexane, benzene, toluene or xylene, weakly polar ethers, for example diethyl ether, tetrahydrofuran or dioxan, or acid amides, for example hexamethylphosphoric acid triamide.

The metallated intermediate need not be isolated, but can be reacted subsequently to the metallating reaction with a reactive compound corresponding to the organic radical $R_a$. The metallating reaction takes place at temperatures of from approximately $-100°$ to approximately $+100°$, preferably below $-30°$. The further reaction can take place at the same temperature and optionally whilst heating slowly to up to $100°$.

For the metallating reaction, it is possible to use both the antipodes of compounds of the formula I and racemic or diastereoisomeric mixtures thereof.

The reactive compound corresponding to the organic radical $R_a$ generally attacks the substrate stereospecifically. If a (4S)-azetidinone of the formula I is used as starting material, a (3R,4S)-4-$R_a$-azetidinone is predominantly obtained. If a (4R)-azetidinone is used, a (3S,4R)-azetidinone of the formula I is predominantly obtained. Therefore it is predominantly a trans compound that is obtained.

In the reaction with a ketone or aldehyde of the formula $R_a'$—(C=O)—$R_a''$, there is formed in the 1-position of the side chain a further chirality centre which customarily has the (R,S)-configuration. A threo-trans compound can be distinguished from an erythro-trans compound with respect to the position of the hydroxy group.

A diastereoisomeric mixture consisting of a threo-trans compound and an erythro-trans compound can be separated into the individual antipodes using the customary methods, for example by fractional crystallisation, by chromatography or similar methods.

In a compound of the formula I that can be obtained according to the process and in which $R_a$ represents an organic radical $R_a$ substituted in the 1-position by hydroxy, for example 1-hydroxyalkyl, a hydroxy group can be protected or substituted in a manner known per se, for example by etherification or esterification.

Suitable protecting groups are acyl radicals of an organic carboxylic or sulphonic acid, especially optionally substituted lower alkanoyl, for example acetyl, trifluoroacetyl, optionally substituted benzyl or phenyl-lower alkanoyl, for example benzoyl, optionally substituted lower alkoxycarbonyl or phenyl-lower alkoxycarbonyl, for example p-nitrobenzyloxycarbonyl, also 2-oxacycloalkyl, for example 2-tetrahydropyranyl, or optionally substituted silyl or stannyl groups, for example trimethylsilyl. A hydroxy-protecting group can be introduced in a manner known per se, for example by treating with reactive derivatives, such as anhydrides, for example acid halides or ketenes, halides, or corresponding unsaturated compounds.

The conversion of compounds of the formula I, in which the index n represents 0, into compounds of the formula I in which n represents 2, is effected by oxidation by treating with agents that convert sulphide groups into sulphone groups, especially with hydrogen peroxide, organic peracids, especially aliphatic percarboxylic acids, for example peracetic acid, perbenzoic acid, chloroperbenzoic acid, for example m-chloroperbenzoic acid, or monoperphthalic acid, with oxidising inorganic acids or salts thereof, for example nitric acid, chromic acid, potassium permanganate or an alkali metal hypochlorite, for example sodium hypochlorite, and also by anodic oxidation. The oxidation is preferably carried out in a suitable inert solvent, for example a halohydrocarbon, for example methylene chloride, chloroform or carbon tetrachloride, an alcohol, for example methanol or ethanol, a ketone, for example acetone, an ether, for example diethyl ether, dioxan or tetrahydrofuran, an amide, for example dimethylformamide, a sulphone, for example dimethyl sulphone, a liquid organic carboxylic acid, for example acetic acid, or in water or a mixture of these solvents, especially a water-containing mixture, for example aqueous acetic acid, at room temperature, or while cooling or gently heating, that is to say, at from approximately $-20°$ to approximately $+90°$, preferably at from approximately $+18°$ to approximately $+30°$. The oxidation can also be carried out stepwise, by first of all oxidising at a low temperature, that is to say, at from approximately $-20°$ to approximately $0°$, until the sulphoxide stage is reached, optionally isolating the sulphoxide stage, and then in a second step oxidising the sulphoxide to form the sulphone, that is to say, to form the 1,1-dioxide of the formula (I), preferably at a higher temperature, such as at room temerature.

For work-up, excess oxidising agent that may possibly still be present can be destroyed by reduction, especially by treating with a reducing agent, such as a thiosulphate, for example sodium thiosulphate.

The starting material of the formula II is manufactured, for example, by reacting an acyloxyazetidinone of the formula

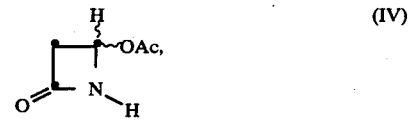

(IV)

wherein Ac represents an acyl radical, with a hydroxy-lower alkyl mercaptan of the formula HS-A-OH in the presence of a suitable base and, if desired, in a resulting compound converting the —S—A—OH group into a different —S—A—OH group and/or, if desired, separating a resulting isomeric mixture of a compound of the formula II into the individual isomers.

In a compound of the formula IV, Ac is an acyl radical of an organic carboxylic or sulphonic acid, especially optionally substituted lower alkanoyl, for example acetyl, trifluoroacetyl or formyl, or optionally substituted benzoyl, for example benzoyl.

A hydroxy-lower alkyl mercaptan contains 2 or 3 carbon atoms between the two hetero atoms and is, for example, 3-mercaptopropanol, or especially 2-mercaptoethanol or 2-mercaptopropan-1-ol.

Suitable bases are strong organic or inorganic bases, for example 1,5-diazabicyclo[5,5,0] undec-5-ene, or alkali metal or alkaline earth metal hydroxides, especially sodium hydroxide. The latter bases are added preferably in concentrated aqueous solutions.

Suitable solvents are weakly polar solvents, for example tetrahydrofuran or dioxan, or relatively strongly polar solvents, for example dimethylformamide, dimethyl sulphoxide, or alcohols, for example methanol or ethanol. The reaction preferably takes place in the presence of water at temperatures of from approximately −20° to approximately 100°, preferably from −10° to room temperature.

In the reaction of an acyloxyazetidinone of the formula IV with a hydroxy-lower alkyl mercaptan a racemic (4R,S)-mixture is obtained. If there is used in this reaction an HS—A—Oh compound, in which A contains a chirality centre, for example (2R)-2-mercaptopropan-1-ol optionally protected at the hydroxy group, then a diastereoisomeric mixture of compounds of the formula II is obtained.

The diastereoisomeric mixture thus obtained can, if desired, be separated into the antipodes as described below.

Compounds of the formula II and the above-mentioned (2R)-2-mercaptopropan-1-ol are new and for their part form, together with their manufacture, a further subject of the present invention.

In the reaction with an acyloxyazetidinone of the formula IV, (2R)-2-mercaptopropan-1-ol is optionally protected at the hydroxyl group by hydroxyl-protecting groups that are customary in cephalosporin or penicillin chemistry. Especially suitable as hydroxyl-protecting groups are silyl groups, for example trimethylsilyl, or acyl groups, for example acetyl groups.

The manufacture of (2R)-2-mercaptopropan-1-ol is effected by esterifying the hydroxy group of an (S)-lactic acid ester in the presence of an organic base, for example triethylamine, by an acid radical of an organic acid, for example the mesyl radical. By reacting the resulting compound with a suitable thio salt, for example potassium thioacetate, the configuration of the lactic acid ester esterified at the hydroxy group is reversed and the esterified hydroxy group is replaced by a substituted thio group. Subsequent reduction with a suitable reducing agent, for example lithium aluminium hydride, yields the (2R)-2-mercaptopropan-1-ol.

Compounds of the formula IV and processes for their manufacutre are known.

The invention relates also to the manufacture of a compound of the formula

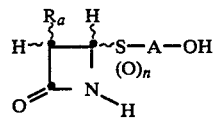

wherein

A and $R_a$ have the meanings given above, and
n has the value 0 or 2, by solvolysing a compound of the formula I, wherein R represents the radical $R_a$, which has the meaning given under formula I, A, $R_b$ and $R_c$ have the meanings given under formula I, and in which n has the value 0 or 2, in the preseence of a suitable solvolysis reagent, and, if desired, converting a compound of the formula V thus obtained and in which n represents 0, into a compound of the formula V in which n represents 2 and/or, separating a compound thus obtained according to the process into the individual isomers.

Suitable solvolysis reagents are, for example, organic acids, for example lower alkanecarboxylic acids, for example glacial acetic acid or formic acid, anhydrides of lower alkanecarboxylic acids, for example acetic anhydride, or sulphonic acids, for example p-toluenesulphonic acid, mineral acids, for example sulphuric or hydrochloric acid, lower alkanols, for example methanol or ethanol, or lower alkanediols, for example ethylene glycol.

The afore-mentioned solvolysis reagents are added undiluted or diluted with water. The solvolysis can also be carried out with pure water.

The solvolysis with the acid reagent preferably takes place in an aqueous solution of this reagent and at temperatures of from approximately −20° to approximately 150°, preferably at from room temperature to 110°.

The sulphide (n=0) or the sulphone (n=2) of the formula I can be solvolysed. If the sulphide is solvolysed, oxidation to form the sulphone takes place subsequently in a manner known per se, for example as described above.

For the separation of diastereoisomeric mixtures that can be obtained according to the invention into the antipodes, physico-chemical methods are suitable, especially fractional crystallisation. It is, however, also possible to use chromatographic methods, especially solid-liquid chromatography. Diastereoisomeric mixtures that are readily volatile can also be separated by distillation or gas chromatography.

One method of separating racemates consists in chromatographing on optically active absorption layers, for example on cane-sugar, or the racemates can be dissolved in optically active solvents and the less easily soluble antipode can be crystallised out, or the different reactivity of the optical antipodes in comparison with biological material such as micro-organisms or isolated enzymes is used, or the racemates are dissolved and one of the optical antipodes is crystallised out by inoculating with a small quantity of an optically active product obtained according to the above methods.

The compounds of the formula V can be converted into 6-substituted 2-penem-3-carboxylic acid compounds, for example as shown in the following reaction scheme and illustrated in the Examples.

The following reaction scheme represents the reaction stages that lead to the product of formula VI.

The $-SO_2-A-OH$ group in a compound of the formula V represents a nucleofugal leaving group and is called W in the following.

Reaction Scheme

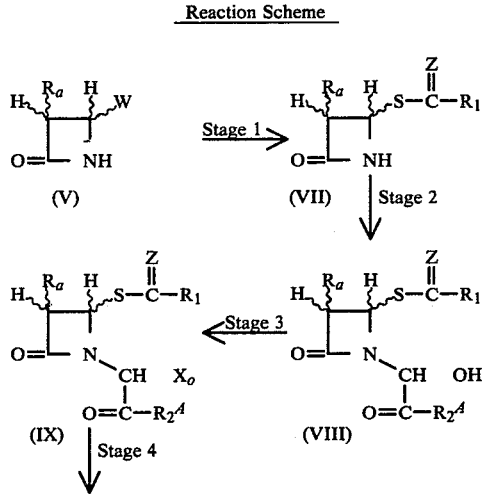

-continued
Reaction Scheme

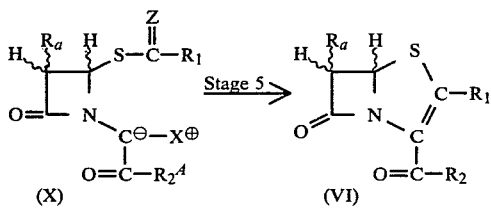

In the compounds of the formulae VII, VIII, IX and X in the reaction scheme, Z is oxygen, sulphur or alternatively, especially when $R_1$ is hydrogen, a methylidene group that is optionally substituted by one or two substituents Y and can be converted by oxidation into an oxo group Z. A substituent Y of this methylidene group is an organic radical, for example one of the organic radicals mentioned under $R_1$, such as one of the aforementioned optionally substituted lower alkyl, cycloalkyl, cycloalkyl-lower alkyl, phenyl or phenyl-lower alkyl radicals, and especially one of the functionally modified, such as esterified, carboxyl groups, including carboxyl groups esterified by an optically active alcohol, such as l-menthol. This methylidene group preferably carries one of the afore-mentioned substituents. Special mention is to be made of the carbomethoxymethylidene group Z. The latter can be used for the manufacture of optically active compounds of the formulae VII, VIII, IX and X.

In a compound of the formula IX, $X_o$ is a reactively esterified hydroxy group, especially halogen or organic sulphonyloxy. In a compound of the formula X, $X^\oplus$ represents one of the phosphonio or phosphono groups customary in the Wittig condensation reaction, especially a triaryl-, for example triphenyl-, or a tri-lower alkyl-, for example tributyl-, phosphonio group, or a phosphono group esterified twice by lower alkyl, for example ethyl, the symbol $X^\oplus$ in the case of the phosphono group additionally including the cation of a strong base, especially a suitable metal ion, such as an alkali metal ion, for example a lithium, sodium or potassium ion. Group $X^\oplus$ is preferably triphenylphosphonio, on the one hand, and, on the other hand, diethylphosphono together with an alkali metal ion, for example a sodium ion.

The 6-substituted-2-penem-3-carboxylic acid compounds that can be manufactured from compounds of the formula V are especially those of the formula

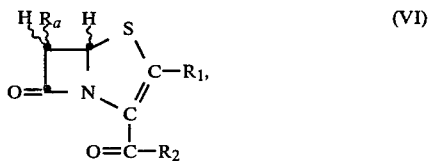

wherein
  $R_a$ represents an organic radical bonded to the ring carbon atom via a carbon atom,
  $R_1$ represents hydrogen, an organic radical bonded to the ring carbon atom via a carbon atom or represents an etherified mercapto group, and
  $R_2$ represents hydroxy or a radical $R_2^A$ that, together with the carbonyl grouping —C(=O)—, forms a protected carboxyl group, and salts of such compounds having salt-forming groups.

2-penem compounds may display valuable pharmacological properties. Thus compounds of the formula VI, in which $R_a$ and $R_1$ have meanings give above and $R_2$ represents hydroxyl or an etherified hydroxy group $R_2^A$ that, togther with the carbonyl group, forms an esterified carboxyl group that preferably can readily be split under physiological conditions, or pharmacologically acceptable salts of such compounds having salt-forming groups, display antibacterial activity. They inhibit for example the growth of gram-positive and gram-negative germs, such as *Staphylococcus aureus* and penicillin-resistant *Staphylococcus aureus, Escherichia coli, Proteus vulgaris, Pseudomonas aeruginos* and *Pseudomonas aeruginosa R.* In a disc plate test using compounds of the formula I according to the invention and the aforementioned germs with a 0.5% solution on filter paper (6 mm diameter), inhibition zones of from approximately 12 to 33 mm diameter are observed.

Penicillin V, tested simultaneously and in analogous manner, causes in the case of penicillin-sensitive *Staphylococcus aureus* germs, inhibition zones of 29 to 33 mm diameter and in the case of penicillin-resistant germs, inhibition zones of at most 9 to 12 mm. Neither penicillin V nor penicillin G is effective against *Pseudomonas aeruginosa*.

The anti-bacterial action in vitro can also be observed in an agar-dilution test (according to Ericsson), there being obtained MIC values of from 0.06 to 8 mcg/ml against gram-positive and gram-negative cocci and MIC values of from 2 to 128 mcg/ml against gram-negative bacilli, such as enterobacteria, Pseudomonas and Haemophilus.

In vivo, in the systemic infection of mice with *Streptococcus pyogenes* Aronson, subcutaneous administration of compounds according to the invention produces $ED_{50}$ values of approximately $\leq 1$ to approximately 50 mg/kg.

Special mention is to be made of the effectiveness against Pseudomonas aeruginosa.

The compounds inhibit β-lactamases and act synergistically in combination with other β-lactam antibiotics.

These compounds or their pharmacologically acceptable salts can be used alone or in combination with other antimicrobic substances, for example in the form of antibiotically active preparations, for the treatment of corresponding systemic or organ infections, also as animal foodstuff additives, for preserving foodstuffs or as disinfectants.

The manufacture of the compounds of the formula VI from the compounds of the formula V is described in European Patent application No. 79 100 258.7.

The following Examples serve to illustrate the invention. Temperatures are given in degrss Centigrade. The following abbreviation is used:
TLC=thin layer chromatogram on silica gel.
The numbering system of the bicyclic compounds is as follows:

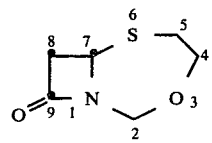

EXAMPLE 1: 4-(2-hydroxyethylthio)-2-oxoazetidine

At −10° and under a nitrogen atmosphere, 10 ml (0.142 mol) of 2-mercaptoethanol are added, while stirring, to a solution of 12.9 g (0.1 mol) of 4-acetoxyazetidin-2-one (manufactured according to K. Clauss et al., Lieb. Ann. Chem., 1974, 539; racemic, m.p. 34°) in 75 ml of 95% ethanol and at −10° 55 ml of 2.0N aqueous sodium hydroxide solution are added dropwise thereto within a period of 30 minutes and the mixture is stirred for 60 minutes at 0°. The mixture is neutralised with 2 ml of trifluoroacetic acid and evaporated to dryness in a vacuum rotary evaporator. The residue is dried in a high vacuum, 100 g of sodium sulphate are added thereto and extraction is carried out twice with 200 ml of methylene chloride each time and then twice with 200 ml of chloroform each time. The combined extracts are filtered and the filtrate is concentrated by evaporation. The viscous residue is further used with purification.

TLC: $R_f$=0.12 (ethyl acetate);

IR spectrum ($CH_2Cl_2$): absorption bands at 3580, 3380, 1770 $cm^{-1}$.

EXAMPLE 2: 1. (4R)- and (4S)-4-((2R)-1-hydroxyprop-2-ylthio)-2-azetidinone.

At −20° a solution of 3.6 ml of diazabicyclo[5,4,0]-undec-5-ene in 6 ml of tetrahydrofuran is added dropwise, while stirring, over a period of 30 minutes to a mixture of 2.58 g (20 mmol) of 4-acetoxyazetidin-2-one and 2.76 g (30 mmol) of (2R)-2-mercaptopropan-1-ol in 12 ml of dry tetrahydrofuran. The reaction mixture is then stirred for a further 30 minutes at −20° and at −40° 0.5 ml of trifluoroacetic acid is added thereto. The mixture is then concentrated in a rotary evaporator at 11 mm and 25° and the residue is chromatographed on 150 g of Merck silica gel with EtOAc/toluene 2 : 1 (20 fractions, each 100 ml) and a 1 : 1 mixture of the two diastereoisomeric title compounds is obtained.

2. The starting material (2R)-2-mercaptopropan-1-ol is manufactured as follows:

2.1. (2S)-2-methylsulphonyloxypropionic acid ethyl ester.

At room temperature and while stirring continuously, 15.5 ml of methanesulphonyl chloride are added dropwise to a mixture of 23.6 g (22.9 ml, 0.2 mol) of (S)-lactic acid ethyl ester and 21.8 ml (0.3 mol) of triethylamine in 400 ml of dry ether, so that the temperature does not exceed 30°. The reaction mixture is then stirred for a further 60 minutes at 25°. The precipitate produced is removed by filtration and the filtrate is washed in succession with 250 ml of aqueous 1N HCL and 250 ml of water. The organic phase is dried over sodium sulphate, the mixture is filtered and the solvent is removed in a rotary evaporator. The residue of 32.4 g is distilled in a high vacuum at 0.05 mm. Boiling point 75° C./0.05 mm.

$R_f$ value: 0.60 (EtOAc).

NMR spectrum (CDCL$_3$) in ppm. 5.2, 1H, q, J=7.5 Hz; 4.35, 2H, q, J=8 Hz; 3.2, 3H s; 1.7, 3H, d, J=7.5 Hz; 1.35, 3H, t, J=8 Hz.

$[\alpha]_D^{20}$: −65° (undiluted).

2.2. (2R)-2-acetylthiopropionic acid ethyl ester.

17.1 g of solid potassium thioacetate are introduced, while stirring mechanically over a period of 15 minutes, into a solution of 19.6 g (2S) -2-methylsulphonyloxypropionic acid ethyl ester in 200 ml of dry tert.-butanol.

The reaction mixture is refluxed for a further 15 minutes. When the reaction mixture has cooled down, 1000 ml of ether are added and the mixture is washed twice with 600 ml of water each time. The organic phase is dried over sodium sulphate and after filtration the solvent is removed in a rotary evaporator. The residue is distilled at 11 mm. The product has a boiling point of from 90° to 95° at 11 mm.

$R_f$ value: 0.63 (EtOAc).

IR spectrum in $CH_2Cl_2$, $cm^{-1}$: 2970, 1732, 1695, 1180.

NMR spectrum in CDCl$_3$ in ppm: 4.2 3H, m; 2.3, 3H, s; 1.45, 3H, d, J=7.5 Hz; 1.25, 3H, t, J=7 Hz.

$[\alpha]_D^{20}$: −48° (undiluted).

2.3. (2R)-2-mercaptopropan-1-ol

In a 750 ml sulphonating flask having a mechanical stirrer, a solution of 14.1 g of acetylthiopropionic acid ethyl ester in 40 ml of dry tetrahydrofuran is added dropwise, within a period of 30 minutes and at a bath temperature of 75° (reflux) to a mixture of 12.16 g of lithium aluminium hydride in 160 ml of dry tetrahydrofuran, and the reaction mixture is relfuxed for a further 60 minutes. After the mixture has cooled, 160 ml of 2N aqueous HCl are added dropwise while stirring continuously and at a bath temperature of 0°, so that the internal temperature does not exceed 30°. After stirring for one hour at room temperature, the mixture is filtered through a fine glass filter and the residue is washed with 700 ml of tetrahydrofuran. The combined filtrates are then concentrated in a rotary evaporator at 25° and 11 mm. 500 ml of methylene chloride are then added to the residue and the mixture is dried with 200 g of sodium sulphate. By filtering and again concentrating the filtrate by evaporation at 25° and 11 mm a liquid residue is produced. The residue is distilled at 11 mm. A pure product is obtained having a boiling point of 56° at 11 mm.

$R_f$ value : 0.15 ($CH_2Cl_2$).

IR spectrum in $CH_2Cl_2$, $cm^{-1}$: 3570, 2920, 2860, 1450, 1390, 1055, 1025.

NMR spectrum in CDCl$_3$ in ppm: 3.3–3.9, 2H, m; 3.3, 1H, m; 2.2, 1H, broad s; 1.45, 1H, d, J=7.5 Hz; 1.3, 3H, d, J=7 Hz.

$[\alpha]_D^{20}$: −10.4° (undiluted).

$[\alpha]_D^{20}$: −25° (CHCl$_3$, c=12).

EXAMPLE 3: (4R)- and (4S)-4-((2R)-1-hydroxyprop-2-ylthio)-2-azetidinone

A solution of 243 mg (1.6 mmol) of diazabicyclo-[5,4,0]undec-5-ene in 0.8 ml of tetrahydrofuran is added, while stirring, over a period of 15 minutes and at −30° to a mixture of 258 mg (2 mmol) of 4-acetoxyazetidin-2-one and 319 mg (2.4 mmol) of 1-acetoxy-(2R)-2-mercaptopropane in 1.2 ml of dry tetrahydrofuran. The mixture is then stirred for 30 minutes at 0°. 25 ml of EtOAc are added, the mixture is washed with 25 ml of 1N aqueous HCl and with 25 ml of saturated aqueous NaHCO$_3$ solution, the organicphase is dried, filtration is carried out and the filtrate is concentrated by evaporation of the solvent in vacuo, yielding a mixture of the diastereoisomeric acetates. The mixture is dissolved in 20 ml of methanol and 1.5 ml of a 10% aqueous K$_2$CO$_3$ solution are added thereto and the whole is stirred for 150 minutes at room temperature; 120 μl of trifluoroacetic acid are then added and the mixture is concentrated in a vacuum rotary evaporator. The residue is dried in a high vacuum at room temerature and then chromatographed on 12 g of Merck silica gel with toluene/E- tOAc 1 : 2 (20 fractions, each 8 ml). A mixture of the two title compounds is obtained.

2. The starting material 1-acetoxy-(2R)-2-mercaptopropane can be obtained in the following manner:

A mixture of 920 mg of the (2R)-2-mercaptopropan-1-ol manufactured according to Example 2, under 2.3, and 1.12 g of acetic anhydride is refluxed for 30 minutes at a bath temperature of 130°. Concentrating in vacuo at 11 mm and 25° yields 1.4 g of liquid residue. The residue is chromatographed on 70 g of Merck silica gel with methylene chloride (15 fractions, each 50 ml).

$R_f$ value: 0.5 (toluene/EtOAc 2 : 1).

IR spectrum in $CH_2Cl_2$, $cm^{-1}$: 2950, 1735, 1230.

NMR spectrum in $CDCl_3$ in ppm: 4.1, 2H, d, J=7 Hz; 3.2, 1H, m; 2.1, 3H, s; 1.65, 1H, d, J=7 Hz; 1.35, 3H, d, J=7 Hz.

EXAMPLE 4: 1. (4R)- and (4S)-4-((2R)-1-hydroxyprop-2-ylthio)-2-azetidinone

A solution of 304 mg (2 mmol) of diazabicyclo[5,4,0]undec-5-ene in 0.8 ml of tetrahydrofuran is added at −30°, while stirring, over a period of 15 minutes to a mixture of 258 mg (2 mmol) of 4-acetoxyazetidin-2-one and 401 mg (2.4 mmol) of 1-trimethylsilyloxy-(2R)-2-mercaptopropane in 1.2 ml of dry tetrahydrofuran. The mixture is then stirred for 30 minutes at 0°. 25 ml of EtOAc are added, the mixture is washed with 20 ml of 0.1N aqueous HCl solution and 25 ml of saturated aqueous $NaHCO_3$ solution, the organic phase is dried over sodium sulphate and the solvent is concentrated by evaporation in vacuo, yielding the diastereoisomeric trimethyl silyl ethers. These ethers are dissolved in 20 ml of methanol and 1 ml of 2N aqueous HCl solution is added and the mixture is stirred for 60 minutes at room temperature. After the addition of 168 mg (2 mmol) of solid $NaHCO_3$, the mxture is concentrated in a vacuum rotary evaporator and the residue is dried in a high vacuum. Chromatography on 12 g of Merck silica gel with toluene/EtOAc 1:2 (20 fractions, each 8 ml) yields a mixture of the two title compounds.

2. The starting material 1-trimethylsilyloxy-(2R)-2-mercaptopropane can be obtained as follows:

1.53 ml of triethylamine are added, while stirring, at 0° and within a period of 15 minutes to a mixture of 920 mg of the (2R)-2-mercaptopropan-1-ol manufactured according to Example 2 under 2.3 and 1.36 ml of trimethylchlorosilane in 10 ml of dry benzene. The mixture is stirred for a further 15 minutes at room temperature and for 15 minutes at 60° and is then cooled and the precipitate formed is filtered off. The filter residue is washed with 10 ml of benzene and the combined filtrates are removed in a rotary evaporator at 11 mm and 25°. Bulb tube distillation of the residue at 11 mm and 100° yields a pure liquid product.

IR spectrum in $CH_2Cl_2$, $cm^{-1}$: 2950, 1080, 875, 845.

NMR in benzene-d, ppm: 3.35, 2H, m; 2.8, 1H, m; 1.4, 1H, d, J=7 Hz; 1.15, 3H, d, J=7 Hz; O, 9H, s.

EXAMPLE 5: (4R)-4-((2R)-1-hydroxyprop-2-ylthio)-2-azetidinone and (4S)-4-((2R)-1-hydroxy-2-propylthio)-2-azetidinone.

The diastereoisomeric mixture can be separated by chromatography: 3.2 g separated in parts on 400 g of Merck silica gel with EtOAc/toluene 2: 1 (20 fractions, each 300 ml) and EtOAc (10 fractions each 300 ml). Fractions 10–11 contain 410 mg of pure 4(S)-isomer.

$R_f$ value: 0.18 (EtOAc).

NMR spectrum in $CDCl_3$ in ppm: 7.2, 1H, broad s; 4.90, 1H, dd, J=3 Hz, J=Hz; 2.6–4.0, 5H, m; 1.26, 3H, d, J=7 Hz.

Fractions 12–17 contain both diastereoisomers and fractions 18–30 contain 400 mg of pure 4(R) compound.

$R_f$ value: 0.15 (EtOAc).

NMR spectrum in $CDCl_3$ in ppm: 7.0, 1H, broad s; 5.0, 1H, dd, J=3 Hz, J=5 Hz; 2.5–3.8, 5H, m; 1.35, 3H, d, J=7 Hz.

EXAMPLE 6: 2,2-dimethyl-9-oxo-3-oxa-6-thia-1-azabicyclo-[5,2,0$^{1,7}$]-nonane.

15 g of the 4-(2-hydroxyethylthio)-2-oxoazetidine that can be obtained according to Example 1 are dissolved in 100 ml of ethanol-free methylene chloride and, at −10°, 26.2 g (30.5 ml, 0.25 mol) of acetone dimethyl ketal are added thereto. 2 ml of boron trifluoride etherate are added, while stirring, at −10° and the mixture is stirred for 30 minutes at −10° and for 2 hours at room temperature. The mixture is then diluted with 150 ml of methylene chloride and washed with 350 ml of ice-cold aqueous saturated sodium bicarbonate solution. The organic phase is dried over sodium sulphate, filtered and freed of the solvent in a vacuum rotary evaporator and then dried in a high vacuum. The solid residue is recrystallised from ether/n-hexane. Melting point of the racemic title compound 67°–68°.

$R_f$: 0.5 (ethyl acetate);

IR spectrum ($CH_2Cl_2$): absorption bands at 1750, 1345, 1240, 1080 $cm^{-1}$.

EXAMPLE 7: (7R,5R)-2,2,5-trimethyl-9-oxo-3-oxa-6-thia-1-azabicyclo[5,2,0$^{1,7}$]nonane.

166 mg of the (4R)-4-((2R)-1-hydroxyprop-2-ylthio)-2-azetidinone that can be obtained according to Example 5 are dissolved in a mixture of 1 ml of dry, ethanol-free methylene chloride and 0.31 ml of acetone dimethyl acetal. 20 μl of boron trifluoride ethyl etherate are added, while stirring, at −10° and the mixture is stirred for 30 minutes at −10° and for 150 minutes at room temperature. The mixture is diluted with 10 ml of methylene chloride, washed with 10 ml of saturated aqueous $NaHCO_3$ solution, the organic phase is dried over sodium sulphate, filtration is carried out and the filtrate is concentrated by evaporation of the solvent, yielding 225 mg of a non-crystalline residue. By chromatographing on 7 g of Merck silica gel with toluene/EtOAc 4: 1 (20 fractions, each 3.5 ml) the pure title compound is produced.

Melting point 87° (n-hexane).

$R_f$: 0.57 (EtOAc).

NMR spectrum in $CDCl_3$ in ppm: 5.17, 1H, dd, J=3 Hz, J=5 Hz; 2.4–4.6, 5H, m; 1.77, 3H, s; 1.50, 3H, s; 1.47, 3H, d, J=7 Hz.

$[\alpha]_D^{20}$: +131° ($CHCl_3$, c=1).

EXAMPLE 8: (7S,5R)-2,2,5-trimethyl-9-oxo-3-oxa-6-thia-1-azabicyclo[5,2,0$^{1,7}$]nonane.

The pure title compound is obtained in a manner analogous to Example 7 from 166 mg of the (4S)-4-

((2R)-1-hydroxyprop-2-ylthio)-2-azetidinone that can be obtained according to Example 5.

Melting point 54° (n-hexane).

$R_f = 0.57$ (EtOAc).

NMR spectrum in CDCl$_3$ in ppm: 5.17, 1H, dd, J=3 Hz, J=5 Hz; 2.4–4.6, 5H, m; 1.75, 3H, s; 1.47, 3H, s; 1.15, 3H, d. J=7 Hz.

$[\alpha]_D^{20}$: $-133°$ (CHCl$_3$, c=1).

EXAMPLE 9:
2,2-dimethyl-trans-8-(1-hydroxyethyl)-9-oxo-3-oxa-6-thia-1-azabicyclo[5,2,0$^{1,7}$]nonane At $-65°$ and under nitrogen 55 ml of a 2.0M solution of a 2.0 M solution of n-butyllithium in n-hexane (0.11 mol) are added dropwise, while stirring, within a period of 15 minutes to a solution of 11.0 g (15.5 ml, 0.11 mol) of diisopropylamine in 200 ml of dry tetrahydrofurane and the mixture is stirred for 15 minutes at $-65°$. A solution of 18.7 g (0.1 mol) of the 2,2-dimethyl-9-oxo-3-oxa-6-thia-1-azabicyclo[5,2,0$^{1,7}$]nonane that can be obtained according to Example 6 in 80 ml of dry tetrahydrofurane is then added, within a period of 15 minutes, while stirring, at $-65°$. The mixture is stirred for a further 10 minutes at $-65°$. Thereafter at $-65°$ 17 ml (0.3 mol) of acetaldehyde in 80 ml of dry tetrahydrofuran are added dropwise over a period of 15 minutes. The temperature of the mixture is allowed to increase slowly to 0° and is stirred for 1.5 hours at 0°. The reaction mixture is poured onto 1 kg of ice and extracted with 2.5 l of methylene chloride; the organic phase is dried over sodium sulphate, filtered and the solvent is removed in a vacuum rotary evaporator. The residue is chromatographed on 1 kg of Merck silica gel with toluene/ethyl acetate (2:1) as eluant (twenty 500 ml fractions). After evaporating off the solvent a viscous mixture of the erythro-trans title compound (2 parts) and the threo-trans title compound (1 part) is obtained.

$R_f = 0.4$ (ethyl acetate).

IR spectrum (CH$_2$Cl$_2$): absorption bands at 3550, 1740, 1220, 1080 cm$^{-1}$.

EXAMPLE 10:
(7R,5R)-2,2,5-trimethyl-trans-8-(1-hydroxyethyl)-9-oxo-3-oxa-6-thia-1-azabicyclo[5.2.0$^{1,7}$]nonane This compound is obtained in a manner analogous to Example 9 by reacting the metallated (7R,5R)-2,2,5-trimethyl-9-oxo-3-oxa-6-thia-1-azabicyclo[5,2,0$^{1,7}$]nonane (see Example 7) with acetaldehyde.

EXAMPLE 11:
2,2-dimethyl-trans-8-hydroxymethyl-9-oxo-3-oxa-6-thia-1-azabicyclo[5,2,0$^{1,7}$]nonane A 2.0 M solution of n-butyllithium in n-hexane (0.11 mol) is added dropwise, while stirring, at $-65°$ and under nitrogen to a solution of 11.0 g (15.5 ml, 0.11 mol) of diisopropylamine in 200 ml of dry tetrahydrofurane. The mixture is stirred 15 minutes at $-65°$. Within 15 minutes, a solution of 18.7 g (0.1 mol) 2,2-dimethyl-9-oxo-3-oxa-6-thia-1-azabicyclo[5,2,0$^{1,7}$]nonane (see Example 6) in 80 ml of dry tetrahydrofurane is then added dropwise, while stirring, at $-65°$. The mixture then is stirred further 10 minutes at $-65°$. Formaldehyde gas is generated in a separate flask by heating up to 150° the formaldehyde-cyclohexanol adduct which is prepared in a conventional manner by reacting an aqueous solution of formaldehyde with cyclohexanol. An excess amount of dry formaldehyde gas is then slowly passed over the reaction mixture at $-65°$. The mixture is stirred 30 minutes at $-65°$. The cold reaction mixture is poured onto a mixture of 250 g ice and 250 g water. 250 ml chloroform and 110 ml 2.0 N hydrochloric acid are added. After shaking the mixture the organic layer is separated. After adding 60 g of sodium chloride the aqueous layer is subsequently extracted two times with chloroform. The organic solution is dried over sodium sulfate and filtered. The solvent is removed by evaporation. The residue obtained is a yellowish oily liquid.

EXAMPLE 12:
(7 R,5R)-2,2,5-trimethyl-trans-8-hydroxymethyl-9-oxo-3-oxa-6-thia-1-azabicyclo[5,2,0$^{1,7}$]nonane This compound is obtained in a manner analogous to Example 11 by reacting the metallated (7R,5R)-2,2,5-trimethyl-9-oxo-3-oxa-6-thia-1-azabicyclo[5,2,0$^{1,7}$]nonane (see example 7) with formaldehyde.

EXAMPLE 13:
2,2-dimethyl-trans-8-allyl-9-oxo-3-oxa-6-thia-1-azabicyclo[5,2,0$^{1,7}$]nonane At $-70°$ 1.8 ml of a 2N solution of butyllithium in n-hexane are added to a solution of 0.35 g (0.5 ml, 3.5 mmol) of diisopropylamine in 5 ml of dry tetrahydrofurane. After 10 minutes a solution of 2,2-dimethyl-9-oxo-3-oxa-6-thia-1-azabicyclo[5,2,0$^{1,7}$]nonane (0.56 g, 3 mmol) in 5 ml of tetrahydrofurane is added. After further 10 minutes 1.1 g (0.8 ml, 9 mmol) of allyl bromide are added and the mixture is stirred for 2 hours at 0°. The mixture is diluted with 100 ml of EtOAc, washed with 20 ml of 1N NaH$_2$PO$_4$ solution and then with 20 ml of water and the organic phase is dried over sodium sulphate. After evaporating off the solvent in vacuo the residue is chromatographed on 25 g of Merck silica gel (toluene/EtOAc 9:1) and the pure title compound is obtained.

$R_f$ value: 0.5 (toluene/EtOAc 1:1).

NMR spectrum (CDCl$_3$ in ppm): 2.3–6.3, 8H, m; 1.7, 3H, s; 1.45, 3H, s.

EXAMPLE 14:
2,2-dimethyl-trans-8-(1-p-nitrobenzyloxycarbonyloxyethyl)-9-oxo-3-oxa-6-thia-1-azabicyclo[5,2,0$^{1,7}$]nonane.

At $-10°$, 21.6 g (0.1 mol) of solid chloroformic acid p-nitrobenzyl ester are added to a solution of 17.4 g (75 mmol) of 2,2-dimethyl-trans-8-(1-hydroxyethyl)-9-oxo-3-oxa-6-thia-1-azabicyclo[5,2,0$^{1,7}$]nonane (see Example 9) in 200 ml of ethanol-free methylene chloride. At $-10°$ 12.2 g (0.1 mol) of solid 4-dimethylaminopyridine are added to the solution in small portions within a period of 30 minutes. The reaction mixture is stirred for a further hour at room temperature and then refluxed for 6 hours. After cooling, the mixture is diluted with 1.5 l of methylene chloride and washed with 1 l of cold aqueous NaCl solution. The organic phase is dried over sodium sulphate, filtered and the solvent is removed in a vacuum rotary eveporator. The residue is chromatographed on 1 kg of Merck SiO$_2$ with toluene/ethyl acetate (9:1) as eluant (twenty 500 ml fractions). After removing the solvent a racemic mixture of the erythro-trans and threo-trans title compounds is obtained.

$R_f = 0.4$ (toluene/ethyl acetate 1:1).

IR spectrum (CH$_2$Cl$_2$): absorption bands at 1760, 1750, 1610, 1530, 1355 cm$^{-1}$.

EXAMPLE 15:
(7R,5R)-2,2,5-trimethyl-trans-8-(1-p-nitrobenzyloxycarbonyloxyethyl)-9-oxo-3-oxa-6-thia-1-azabicyclo[5,2,0$^{1,7}$]nonane This compound is obtained in a manner analogous to Example 14 by reacting (7R,5R)-2,2,5-trimethyl-trans-8-(1-hydroxyethyl)-9-oxo-3-oxa-6-thia-1-azabicyclo[5,2,0$^{1,7}$]nonane (see Example 10) with chloroformic acid p-nitrobenzylester in the presence of 4-dimethylaminopyridine.

EXAMPLE 16:
2,2-dimethyl-trans-8-p-nitrobenzyloxycarbonyloxymethyl-9-oxo-3-oxa-6-thia-1-azabicyclo[5,2,0$^{1,7}$]nonane 21.6 g (0.1 mol) of solid chloroformic acid p-nitrobenzyl ester is added at −10° to a solution of 22 g crude 2,2-dimethyl-trans-8-hydroxymethyl-9-oxo-3-oxa-6-thia-1-azabicyclo[5,2,0$^{1,7}$]nonane (see example 11) in 250 ml of methylene chloride. 12.2 g (0.1 mol) of solid 4-dimethylaminopyridine are added to the solution in small portions within 30 minutes. The mixture is stirred 4 hours at 3° to 5°. The cold mixture is washed with 200 ml of 0.5 N aqueous hydrochloric acid and an aqueous sodium chloride solution.

The organic phase is dried over sodium sulphate and filtered. The solvent is removed by evaporation. The residue obtained is a yellow foam. Recristallisation from Isopropanol yields a solid. Melting point 82° C.

EXAMPLE 17:
(7R,5R)-2,2,5-trimethyl-trans-8-p-nitrobenzyloxycarbonyloxymethyl-9-oxo-3-oxa-6-thia-1-azabicyclo[5,2,0$^{1,7}$]nonane This compound is obtained in a manner analogous to Example 16 by reacting (7R,5R)-2,2,5-trimethyl-trans-8-hydroxymethyl-9-oxo-3-oxa-6-thia-1-azabicyclo[5,2,0$^{1,7}$]nonane (see Example 12) with chloroformic acid p-nitrobenzyl ester in the presence of 4-dimethylaminopyridine.

EXAMPLE 18:
2,2-dimethyl-trans-8-(1-p-nitrobenzyloxycarbonyloxyethyl)-9-oxo-3-oxa-6-thia-1-azabicyclo[5,2,0$^{1,7}$]nonane-6-dioxide At −10° 19.4 g (0.1 mol) of m-chloroperbenzoic acid (90%) are added in small portions within a period of 30 minutes to a solution of 16.4 g of the 2,2-dimethyl-trans-8-(1-p-nitrobenzyloxycarbonyloxyethyl)-9-oxo-3-oxa-6-thia-1-azabicyclo[5,2,0$^{1,7}$]nonane that can be obtained according to Example 14 in 200 ml of dry methylene chloride.

The mixture is then stirred for 1 hour at 0°, diluted with 1.5 l of methylene chloride and washed with saturated aqueous sodium bicarbonate solution, 10% sodium bisulphite solution and again with saturated sodium bicarbonate solution. The organic phase is dried over sodium sulphate and the solvent is evaporated off in a vacuum rotary evaporator. The non-crystalline residue consists of a racemic mixture of erythro-trans and threo-trans title compounds and is used further directly.

$R_f$=0.6 (EtOAc).

IR spectrum (CH$_2$Cl$_2$): absorption bands at 1780, 1750, 1610, 1325, 1135 cm$^{-1}$.

EXAMPLE 19:
(7R,5R)-2,2,5-trimethyl-trans-8-(1-p-nitrobenzyloxycarbonyloxyethyl)-9-oxo-3-oxa-6-thia-1-azabicyclo[5,2,0$^{1,7}$]nonane-6-dioxide This compound is obtained in a manner analogous to Example 18 by reacting (7R,5R)-2,2,5-trimethyl-trans-8-(1-p-nitrobenzyloxycarbonyloxyethyl)-9-oxo-3-oxa-6-thia-1-azabicyclo[5,2,0$^{1,7}$]nonane (see Example 15) with m-chloroperbenzoic acid.

EXAMPLE 20:
2,2-dimethyl-trans-8-p-nitrobenzyloxycarbonyloxymethyl-9-oxo-3-oxa-6-thia-1-azabicyclo[5,2,0$^{1,7}$]nonane-6-dioxide 47.8 g (0.25 mol) of m-chloroperbenzoic acid are added within 30 minutes at −10° in small portions to a solution of ca. 40 g 2,2-dimethyl-trans-8-p-nitrobenzyloxycarbonyloxymethyl-9-oxo-3-oxa-6-thia-1-azabicyclo[5,2,0$^{1,7}$]nonane (see Example 16) in 500 ml methylene chloride.

The mixture is then stirred for 1 hour at 0° and is washed with saturated aqueous sodium bicarbonate solution, 10% sodium bisulfite solution and again with saturated aqueous sodiumbicarbonate solution. The organic phase is dried over sodium sulfate and filtered. The solvent is removed by evaporation. The residue obtained is a solid which is recristallised from isopropanol. Melting point 158°.

EXAMPLE 21:
(7R,5R)-2,2,5-trimethyl-trans-8-p-nitrobenzyloxycarbonyloxymethyl-9-oxo-3-oxa-6-thia-1-azabicyclo[5,2,0$^{1,7}$]nonane-6-dioxide This compound is obtained in a manner analogous to Example 20 by reacting (7R,5R)-2,2,5-trimethyl-trans-8-p-nitrobenzyloxycarbonyloxymethyl-9-oxo-3-oxa-6-thia-1-azabicyclo[5,2,0$^{1,7}$]nonane (see Example 17) with m-chloroperbenzoic acid.

EXAMPLE 22:
trans-3-(1-p-nitrobenzyloxycarbonyloxyethyl)-4-(2-hydroxyethylsulphonyl)-2-oxoazetidine.

17.7 g (40 mmol) of crude 2,2-dimethyl-trans-8-(1-p-nitrobenzyloxycarbonyloxyethyl)-9-oxo-3-oxa-6-thia-1-azabicyclo[5,2,0$^{1,7}$]nonane 6-dioxide (see Example 18) are dissolved in 260 ml of glacial acetic acid and diluted with 60 ml of water. The mixture is refluxed for 105 minutes, freed of solvent in a vacuum rotary evaporator and dried in a high vacuum. The residue is dissolved in 60 ml of methylene chloride and crystallised at −20°. The pure erythro-trans title compound is obtained by further recrystallisation of the crystals.

$R_f$ value: 0.35 (EtOAc).

Melting point 152°.

IR spectrum (CH$_2$Cl$_2$): absorption bands at 3570, 3370, 1790, 1750, 1520, 1350 cm$^{-1}$.

NMR spectrum in (DMSO-d/100 Mc; in ppm): 9.1, 1H, s; 8.3–7.6, 4H, m; 5.3, 2H, s; 5.5–5.0, 1H; 5.1, 1H, dd, J=4 Hz, J=6.5 Hz; 4.9, 1H, d, J=2.5 Hz; 3.7–3.9, 3H, m; 3.3–3.4, 2H, m; 1.5, d, 3H, J=6.5 Hz.

The mother liquor is concentrated by evaporation and the residue is chromatographed on 600 g of Merck SiO$_2$ with toluene/ethyl acetate as eluant (2:1). The fractions having an Rf value of 0.4 (EtOAc) are combined and the solvent is removed in a vacuum rotary evaporator. The pure amorphous threo-trans title compound has an $R_f$ value=0.4 (EtOAc).

IR spectrum (CH$_2$Cl$_2$): absorption bands at 3570, 3370, 1790, 1750, 1520, 1350 cm$^{-1}$.

NMR spectrum in (DMSO-d/100 Mc; in ppm): 9.1, 1H, s; 8.4–7.6, 4H, m; 5.3, 2H, s; 5.5–5.0, 1H, 5.1, 1H, dd, J=5 Hz, J=6.5 Hz; 4.0, 1H, d, J=2.5 Hz; 3.9–3.7, 3H, m; 3.3, 2H, m; 1.45, 3H, d, J=6.5 Hz.

EXAMPLE 23:
(7R,5R)-2,2,5-trimethyl-trans-8-(1-p-nitrobenzyloxycarbonyloxyethyl)-4-(2-hydroxyethylsulfonyl)-2-oxoazetidine This compound is obtained in a manner analogous to Example 22 by hydrolysing (7R,5R)-2,2,5-trimethyl-trans-8-(1-p-nitrobenzyloxycarbonyloxyethyl)-9-oxo-3-oxa-6-thia-1-azabicyclo[5,2,0$^{1,7}$]nonane-6-dioxide (see Example 19) with a solution of acetic acid in water. The pure erythro-trans and threo-trans compounds are separated by fractional crystallisation in methylene chloride.

EXAMPLE 24:
trans-3-p-nitrobenzyloxycarbonyloxymethyl-4-(2-hydroxyethylsulphonyl)-2-oxoazetidine 4.35 g (10 mmol) of 2,2-dimethyl-trans-8-p-nitrobenzyloxycarbonyloxymethyl-9-oxo-3-oxa-6-thia-1-azabicyclo[5,2,0$^{1,7}$]nonane-6-dioxide (see Example 20) are dissolved in 130 ml glacial acetic acid and are diluted with 30 ml water. The temperature of the mixture is maintained at 55° over a period of 4 days. The solvent is removed by evaporation. The residue is dissolved in ethyl acetate and is washed with 30 ml of aqueous sodium bicarbonate solution. The organic layer is separated. The aqueous layer is extracted with ethyl acetate. The organic phase is dried over sodium sulfate and filtered. The solvent is removed by evaporation. A viscous residue is obtained. Purification by chromatography and recrystallisation from isopropanol yields a solid. Melting point 128°.

EXAMPLE 25:
trans-3-p-nitrobenzyloxycarbonyloxymethyl-4-[(2R)-1-hydroxy-2-propylsulphonyl]-2-oxoazetidinone This compound is obtained in a manner analogous to Example 20 by hydrolysing (7R,5R)-2,2,5-trimethyl-trans-8-p-nitrobenzyloxycarbonyloxymethyl-9-oxo-3-oxa-6-thia-1-azabicyclo[5,2,0$^{1,7}$]nonane-6-dioxide (see Example 21) with a solution of glacial acetic acid in water.

The following examples illustrate the further processing of the compounds that can be obtained according to Examples 1 to 25:

EXAMPLE 26:
threo-trans-3-(1-p-nitrobenzyloxycarbonyloxyethyl)-4-(cis-β-methoxycarbonylvinylmercapto)-2-oxoazetidine.

Under a nitrogen atmosphere and while stirring, 48 ml of 1.0N aqueous sodium hydroxide solution are added dropwise, within a period of 5 minutes, to a solution cooled to −15° of 4.73 g (24 mmol) of cis-β-methoxycarbonylvinylisothiuronium chloride in 100 ml of 95% ethanol, the internal temperature being maintained at −10° by external cooling. After stirring for a further 5 minutes at −10°, a solution of 8.1 g (20 mmol) of threo-trans-3-(1-p-nitrobenzyloxycarbonyloxyethyl)-4-(2-hydroxyethylsulphonyl)-2-oxoazetidine in 60 ml of 95% ethanol is added dropwise at −10° within a period of 5 minutes, and the mixture is then stirred for 80 minutes at 2°. After adding 1 l of methylene chloride, the mixture is washed twice using 500 ml of saturated aqueous NaCl solution each time; the organic phase is dried over sodium sulphate, filtered and freed of the solvent in a vacuum rotary evaporator. The solid residue is chromatographed on 300 g of Merck SiO$_2$ with toluene-/ethyl acetate as eluant (2:1). After evaporating off the solvent in vacuo, crystallisation from methylene chloride/n-hexane is carried out and the pure title compound is obtained.

R$_f$=0.6 (EtOAc).

Melting point 164.5–165.5°.

IR spectrum (CH$_2$Cl$_2$): absorption bands at 3500, 1790, 1760, 1710, 1530, 1360 cm$^{-1}$.

NMR spectrum (in DMSO-d/100 Mc; in ppm): 8.8, 1H, s; 8.3–7.6, 4H, dd; 7.5, 1H, d, J=10 Hz; 6.0, 1H, d, J=10 Hz; 5.3, 2H, s; 5.1, 1H, d, J=2.5 Hz; 5.2–5.0, 1H, m; 3.6, 3H, s; 3.5, 1H, dd, J=6 Hz, J=2.5 Hz; 1.35, 3H, d, J=6.5 Hz.

EXAMPLE 27:
erythro-trans-3-(1-p-nitrobenzyloxycarbonyloxyethyl)-4-(cris-β-methoxycarbonylvinylmercapto)-2-oxoazetidine.

The title compound is obtained from the corresponding erythro-trans-starting material according to the instructions in Example 26.

R$_f$ value=0.6, (EtOAc).

Melting point 135–137.5°.

IR spectrum (CH$_2$Cl$_2$): absorption bands at 3400, 1790, 1760, 1710, 1530, 1360 cm$^{-1}$.

NMR spectrum (in DMSO-d/100 Mc; in ppm): 8.8, 1H, s; 8.3–7.6, 4H, m; 7.5, 1H, d, J=10 Hz; 6.0, 1H, d, J=10 Hz; 5.3, 2H, s; 5.05, 1H, d, J=2.5 Hz; 5.2–5.0, 1H, m; 3.65, 3H, s; 3.55, 1H, dd, J=2.5 Hz, J=5 Hz; 1.4, 3H, d, J=6.5 Hz.

EXAMPLE 28:
2-[threo-trans-3-(1-p-nitrobenzyloxycarbonyloxyethyl)-4-(cis-β-methoxycarbonylvinylmercapto)-2-oxoazetidinyl]-2-hydroxyacetic acid acetonyl ester.

A mixture of 2.25 g (50 mmol) of threo-trans-3-(1-p-nitrobenzyloxycarbonyloxyethyl)-4-(cis-β-methoxycarbonylvinylmercapto)-2-oxoazetidine and 2 g of glyoxylic acid acetonyl ester is dissolved at 30° in 5 ml of N,N-dimethylformamide and 10 ml of toluene and stirred for 15 hours over a molecular sieve 3 Å. After the mixture has cooled it is filtered, the residue is washed several times with ethyl acetate and the combined filtrates are freed of solvent in a vacuum rotary evaporator. The residue is then concentrated by evaporation several times with dimethylformamide in vacuo (at 0.02 mm Hg) at a bath temperature of 55° and then chromatographed on 120 g of Merck SiO$_2$ with toluene-/ethyl acetate (2:1) as eluant. The fractions that contain the product are combined and freed of solvent in a vacuum rotary evaporator. The amorphous viscous substance has R$_f$=0.6 (EtOAc).

IR spectrum (CH$_2$Cl$_2$): absorption bands at 3500, 1780, 1760, 1740, 1530 cm$^{-1}$.

EXAMPLE 29:
2-[erythro-trans-3-(1-p-nitrobenzyloxycarbonyloxyethyl)-4-(cis-β-methoxycarbonylvinylmercapto)-2-oxoazetidinyl]-2-hydroxyacetic acid acetonyl ester.

The corresponding title compound is obtained from the erythro-trans starting material according to the instructions in Example 28. Amorphous, viscous substance R$_f$=0.6 (EtOAc).

IR spectrum (CH$_2$Cl$_2$): absorption bands at 3500, 1780, 1760, 1740, 1530 cm$^{-1}$.

EXAMPLE 30:
2-[threo-trans-3-(1-p-nitrobenzyloxycarbonyloxyethyl)-4-(cis-β-methoxycarbonylvinylmercapto)-2-oxoazetidinyl]-2-triphenylphosphoranylideneacetic acid acetonyl ester.

At −10° and under a nitrogen atmosphere, 0.43 ml (6 mmol) of thionyl chloride is added, while stirring, to a solution of 2.7 g (5 mmol) of 2-[threo-trans-3-(1-p-nitrobenzyloxycarbonyloxyethyl)-4-(cis-β-methoxycarbonylvinylmercapto)-2-oxoazetidinyl]-2-hydroxyacetic acid acetonyl ester in 25 ml of dry tetrahydrofuran and then, at −10°, 0.83 ml (6 mmol) of triethylamine is added dropwise over a period of 2 minutes. The mixture is stirred for a further 30 minutes at 0°, 150 ml of ice-cold methylene chloride are added thereto and the mixture is subsequently washed with 50 ml of 0.1N aqueous HCl solution and then with 50 ml of saturated salt solution. The organic phase is dried over sodium sulphate, filtered and the solvent is removed in a vacuum rotary evaporator. The amorphous, solid residue is used directly.

The amorphous solid residue (2.8 g, 5 mmol) is dissolved in a mixture of 2.9 g (12 mmol) of triphenylphosphine and 4 ml of tetrahydrofuran and is allowed to stand for 24 hours at room temperature under a nitrogen atmosphere. The mixture is diluted with 100 ml of methylene chloride and washed twice using a 30 ml portion of 10% aqueous soda solution each time. The organic phase is dried over sodium sulphate, filtered and freed of solvent in a vacuum rotary evaporator. The residue is chromatographed on 100 g of Merck SiO$_2$ with toluene/ethyl acetate (3:1) as eluant. The amorphous solid residue has an R$_f$ value=0.5 (EtOAc).

IR spectrum (CH$_2$Cl$_2$): absorption bands at 1755, 1695, 1630, 1525 cm$^{-1}$.

EXAMPLE 31:
2-[erythro-trans-3-(1-p-nitrobenzyloxycarbonyloxyethyl)-4-(cis-β-methoxycarbonylvinylmercapto)-2-oxoazetidinyl]-2-triphenylphosphoranylideneacetic acid acetonyl ester.

The corresponding title compound is also obtained according to the instructions in Example 26 from the erythro-trans starting material.
Amorphous solid.
R$_f$=0.5 (EtOAc).
IR spectrum (CH$_2$Cl$_2$): absorption bands at 1755, 1695, 1630, 1525 cm$^{-1}$.

EXAMPLE 32:
threo-trans-6-(1-p-nitrobenzyloxycarbonyloxyethyl)-penem-3-carboxylic acid acetonyl ester.

1.25 ml of trifluoroacetic acid are added to a solution of 1.96 g (2.5 mmol) of 2-[threo-trans-3-(1-p-nitrobenzyloxycarbonyloxyethyl)-4-(cis-β-methoxycarbonylvinylmercapto)-2-oxoazetidinyl]-2-triphenylphosphoranylideneacetic acid acetonyl ester in 40 ml of methylene chloride at −20° and at this temperature a stream of O$_3$ in O$_2$ (0.33 mmol of O$_3$ per minute) is introduced into the mixture over a period of 15 minutes. Excess O$_3$ is subsequently removed by introducing nitrogen and then 2 ml of dimethyl sulphide are added; the minture is stirred for 10 minutes at 10°, diluted with 50 ml of ice-cold methylene chloride and washed twice using a 25 ml portion of 10% aqueous potassium bicarbonate solution each time; the organic phase is dried over sodium sulphate and concentrated by evaporation in a vacuum rotary evaporator; the solid residue is dried for 2 minutes in a high vacuum and dissolved in 60 ml of methylene chloride (freshly filtered over Alox). The solution is then refluxed for 90 minutes under a nitrogen atmosphere and after cooling is concentrated by evaporation in a vacuum rotary evaporator and the residue is chromatographed on 25 g of Merck SiO$_2$ with toluene/ethyl acetate (3:1) as eluant. After concentrating the combined fractions by evaporation, the pure amorphous title compound is obtained.

R$_f$ value=0.55 (EtOAc).
IR spectrum (CH$_2$Cl$_2$): absorption bands at 1795, 1750, 1745, 1720, 1530, 1350 cm$^{-1}$.
NMR spectrum (in acetone-d/100 Mc; in ppm): 8.3–7.6, 4H, m; 7.6 1H, s; 5.95, 1H, d, J=2.5 Hz; 5.3, 2H, s; 5.4–5.1, 1H, m; 4.8, 2H, s; 4.2, 1H, dd, J=6 Hz, J=2.5 Hz; 2.1, 3H, s; 1.45, 3H, d, J=6.5 Hz.

EXAMPLE 33:
erythro-trans-6-(1-p-nitrobenzyloxycarbonyloxyethyl)-penem-3-carboxylic acid acetonyl ester.

The corresponding title compound is also obtained according to the instructions in Example 32 using the erythro-trans starting compound as starting material.
Melting point 154°–156°.
R$_f$=0.55 (EtOAc).
IR spectrum (CH$_2$Cl$_2$): absorption bands at 1795, 1745, 1720, 1530, 1350 cm$^{-1}$.
NMR spectrum (in acetone-d/100 Mc; ppm): 8.4–7.6, 4H, m; 7.6, 1H, s; 5.8, 1H, d, J=2.5 Hz; 5.35, 2H, s; 5.25, 1H, dd, J=6.5, Hz, J=3.5 Hz; 4.80, 2H, s; 3.8, 1H, m; 2.1, 3H, s; 1.5, 3H, d, J=6.5 Hz.

EXAMPLE 34:
threo-trans-6-(1-hydroxyethyl)penem-3-carboxylic acid acetonyl ester.

A solution of 0.936 g (2 mmol) of threo-trans-6-(1-p-nitrobenzyloxycarbonyloxyethyl)penem-3-carboxylic acid acetonyl ester in 80 ml of a mixture of equal parts of acetonitrile and 95% ethanol is hydrogenated over 800 mg of 10% Pd/C catalyst at room temperature for 2.5 hours. The mixture is filtered, the filtrate concentrated by evaporation and the residue is chromatographed on 40 g of Merck SiO$_2$ with toluene/ethyl acetate 2:1 as eluant. The combined fractions are freed of solvent in a vacuum rotary evaporator and the residue is crystallised by adding methylene chloride/ether.

R$_f$ value=0.4 (EtOAc).
Melting point 115°–116°.
IR spectrum (CH$_2$Cl$_2$): 3580, 1790, 1725, 1720, 1560, 1175 cm$^{-1}$.
NMR spectrum (in acetone-d/100 Mc; ppm): 7.6, 1H, s; 5.85, 1H, d, J=2 Hz; 4.8, 1H, s; 4.4, 1H, m; 4.4–4.0, 1H, s; 3.85, 1H, d, J=7 Hz; J=2 Hz; 2.15, 3H, s; 1.3, 3H, d, J=6.5 Hz.

EXAMPLE 35:
erythro-trans-6-(1-hydroxyethyl)penem-3-carboxylic acid acetonyl ester.

The corresponding title compound is also obtained according to the instructions in Example 34 from the erythro-trans starting compound.
R$_f$=0.4 (EtOAc).
Melting point 120°–121.5°.
IR spectrum (CH$_2$Cl$_2$): absorption bands at 3580, 1790, 1725, 1720, 1560, 1175 cm$^{-1}$.

NMR spectrum (in acetone-d/100 Mc; ppm): 7.55, 1H, d, J=1 Hz; 5.8, 1H, d, J=2 Hz; 4.8, 2H, s; 4.4–4.0, 1H, s; 4.4–4.2, 1H, m; 4.0, 1H, m; 2.15, 3H, s; 1.35, 3H, d, J=6.5 Hz.

EXAMPLE 36:
threo-trans-6-(1-hydroxyethyl)penem-3-carboxylic acid

At 0° and under a nitrogen atmosphere, 10 ml of aqueous 0.1N NaOH solution are added dropwise over a period of 15 minutes to a solution of 0.271 g (1 mmol) of threo-trans-6-(1-hydroxyethyl)penem-3-carboxylic acid acetonyl ester in 40 ml of acetonitrile and 10 ml of water. The mixture is stirred for a further 30 minutes at 0°, then stirred for 5 minutes at 0° with 6 g of swollen weakly acidic cation exchanger IV (Merck), filtered and concentrated by evaporation in vacuo to a volume of approximately 20 ml and chromatographed with water on ten 20 cm×20 cm Antec gel dodecyltrichlorosilane TLC plates. Elution with acetonitrile/H$_2$O (3:1) and lyophilisation of the filtrate yields the sodium salt of the title compound in the form of an amorphous solid.

R$_f$ value=0.4 H$_2$O, Antec gel dodecyltrichlorosilane TLC plates).

IR spectrum (KBr): 1750 cm$^{-1}$.

NMR spectrum (in D$_2$O/100 Mc; ppm): 7.25, 1H, s; 5.95, 1H, d, J=2 Hz; 4.45, 1H, m; 4.15, 1H, dd. J=6 Hz, J=2 Hz; 1.48, 3H, d, J=6.5 Hz.

12 mg of the pure sodium salt are dissolved in 0.5 ml of water and the resulting solution is applied to an ion exchanger column (strongly acidic ion exchanger I, Merck) that contains 0.5 g of washed resin. Elution to neutrality with water and lyophilisation of the acidic fractions yields the pure title compound. The compound is recrystallised from hot acetonitrile.

Melting point 230° (transition at 155°–156°).

R$_f$ value: 0.1 (glacial acetic acid/toluene/water 5:5:1).

IR spectrum (KBr): 3480, 1795, 1670, 1545, 1435, 1255, 1160 cm$^{-1}$.

UV spectrum in ethanol: λ$_{max}$ 260 nm (ε 3850), 311 nm (ε 6400).

EXAMPLE 37:
erythro-trans-6-(1-hydroxyethyl)penem-3-carboxylic acid

The corresponding sodium salt of the title compound is obtained according to the instructions in Example 36 from the erythro-trans starting compound.

Amorphous solid.

R$_f$=0.4 (H$_2$O, Antec gel dodecyltrichlorosilane TLC plates).

IR spectrum (KBr): 1750 cm$^{-1}$.

NMR spectrum (in D$_2$O/100 Mc; ppm): 7.3, 1H, s; 5.9, 1H, d, J=2 Hz; 4.4, 1H, m; 4.2, 1H, dd, J=4 Hz, J=2 Hz; 1.52, d, J=6.5 Hz.

The pure title compound is obtained in similar manner.

Melting point 230° (transition at 147°–151°).

R$_f$ value 0.1 (glacial acetic acid/toluene/water 5:5:1).

IR spectrum (KBr): 3510, 1785, 1670, 1550, 1435, 1260, 1180, 1035, 835 cm$^{-1}$.

UV spectrum in ethanol:λ$_{max}$260 nm (ε 3650), 311 nm (ε 6300).

EXAMPLE 38:

The following compounds can be obtained in a manner analogous to the above Examples using corresponding starting materials and by way of corresponding intermediates.

6-ethyl-2-(2-aminoethylthio)-2-penem-3-carboxylic acid,
6-hydroxymethyl-2-penem-3-carboxylic acid,
6-hydroxymethyl-3-methyl-2-penem-3-carboxylic acid,
6-hydroxymethyl-2-(3-aminopropyl)-2-penem-3-carboxylic acid,
6-hydroxymethyl-2-(3-acetylaminopropyl)-2-penem-3-carboxylic acid,
6-hydroxymethyl-2-ethylthio-2-penem-3-carboxylic acid,
6-hydroxymethyl-2-(2-aminoethylthio)-2-penem-3-carboxylic acid,
6-hydroxymethyl-2-(2-acetylaminoethylthio)-2-penem-3-carboxylic acid,
6-(1-hydroxyethyl)-2-methyl-2-penem-3-carboxylic acid,
6-(1-hydroxyethyl)-2-(3-aminopropyl)-2-penem-3-carboxylic acid,
6-(1-hydroxyethyl)-2-(3-acetylaminopropyl)-2-penem-3-carboxylic acid,
6-(1-hydroxyethyl)-2-ethylthio-2-penem-3-carboxylic acid,
6-(1-hydroxyethyl)-2-(2-aminoethylthio)-2-penem-3-carboxylic acid,
6-(1-hydroxyethyl)-2-(2-acetylaminoethylthio)-2-penem-3-carboxylic acid,
6-(2-hydroxyprop-2-yl)-2-penem-3-carboxylic acid,
6-(2-hydroxyprop-2-yl)-2-methyl-2-penem-3-carboxylic acid,
6-(2-hydroxyprop-2-yl)-2-(3-aminopropyl)-2-penem-3-carboxylic acid,
6-(2-hydroxyprop-2-yl)-2-(3-acetylaminopropyl)-2-penem-3-carboxylic acid,
6-(2-hydroxyprop-2-yl)-2-ethylthio-2-penem-3-carboxylic acid,
6-(2-hydroxyprop-2-yl)-2-(2-aminoethylthio)-2-penem-3-carboxylic acid,
6-(2-hydroxyprop-2-yl)-2-(2-acetylaminoethylthio)-2-penem-3-carboxylic acid,
6-hydroxymethyl-2-(1-1-methyl-1H-tetrazol-5-ylthiomethyl)-2-penem-3-carboxylic acid,
both in racemic and optically active form, and their salts.

EXAMPLE 39:

Dry ampoules or phials containing 0.5 g of the sodium salt of 6-(1-hydroxyethyl)-2-penem-3-carboxylic acid as active substance are manufactured as follows:

| Composition (for 1 ampoule or phial): | |
|---|---|
| Active substance | 0.5 g |
| Mannitol | 0.05 g |

A sterile aqueous solution of the active substance and the mannitol is subjected to freeze-drying under aseptic conditions in 5 ml ampoules or 5 ml phials and the ampoules or phials are sealed and examined.

EXAMPLE 40:

Dry ampoules or phials containing 0.25 g of 6-(1-hydroxyethyl)-2-penem-3-carboxylic acid as active substance are manufactued as follows:

| Composition (for 1 ampoule or phial): | |
|---|---|
| Active substance | 0.25 g |
| Mannitol | 0.025 g |

A sterile aqueous solution of the active substance and the mannitol is subjected to freeze-drying under aseptic conditions in 5 ml ampoules or 5 ml phials and the ampoules or phials are sealed and examined.

We claim:

1. Compounds of the formula

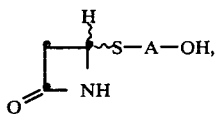

(II)

wherein

A represents a lower alkylene radical having 2 or 3 carbon atoms between the two hetero atoms, the stereoisomers of compounds of the formula II and mixtures of these stereoisomers.

2. Compounds of the formula

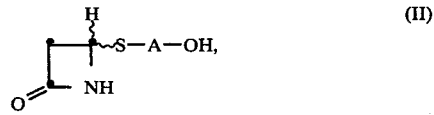

(II)

wherein

A represents a lower alkylene radical having 2 or 3 carbon atoms between the two hetero atoms.

3. 4-(2-hydroxyethylthio)-2-oxoazetidine.

4. (4R)-4-((2R)-1-hydroxyprop-2-ylthio)-2-azetidinone.

5. (4S)-4-((2R)-1-hydroxyprop-2-ylthio)-2-azetidinone.

* * * * *

UNITED STATES PATENT AND TRADEMARK OFFICE
CERTIFICATE OF CORRECTION

PATENT NO. : 4,431,588
DATED : February 14, 1984
INVENTOR(S) : Hans-Rudolf Pfaendler It is certified that error appears in the above-identified patent and that said Letters Patent are hereby corrected as shown below:

Cover page to the left Appl. No.: 480,080, should read -- 430,080 --

Signed and Sealed this

Twenty-second Day of May 1984

[SEAL]

Attest:

GERALD J. MOSSINGHOFF

Attesting Officer

Commissioner of Patents and Trademarks